US00PP20973P2

(12) United States Plant Patent
Danziger

(10) Patent No.: US PP20,973 P2
(45) Date of Patent: May 4, 2010

(54) ***PETUNIA* PLANT NAMED 'DANRAY5'**
(50) Latin Name: *Petunia sensu Wijsman*
Varietal Denomination: DANRAY5

(75) Inventor: Gabriel Danziger, Moshav Nir-Zvi (IL)
(73) Assignee: Danziger "DAN" Flower Farm, Post Beit Dagan (IL)

( * ) Notice: Subject to any disclaimer, the term of this patent is extended or adjusted under 35 U.S.C. 154(b) by 0 days.
(21) Appl. No.: 12/381,321
(22) Filed: Mar. 11, 2009
(51) Int. Cl.
*A01H 5/00* (2006.01)
(52) U.S. Cl. ..... Plt./356
(58) Field of Classification Search ..... Plt./356
See application file for complete search history.

*Primary Examiner*—Annette H Para
(74) *Attorney, Agent, or Firm*—Foley & Lardner LLP

(57) ABSTRACT

A new and distinct *Petunia* plant named 'DANRAY5' characterized by having mounded growth habit; large in size, red-colored flowers; high rate floriferous; early to bloom with long bloom period; and suitable for patios and outdoor beddings.

2 Drawing Sheets

Latin name of the genus and species of the claimed plant: *Petunia sensu Wijsman.*

Variety denomination: 'DANRAY5'.

BACKGROUND OF THE INVENTION

The present invention relates to a new and distinct cultivar of *Petunia* plant, botanically known as *Petunia sensu Wijsman,* hereinafter referred to by the cultivar name 'DANRAY5'.

The new *Petunia* cultivar is a product of a planned breeding program conducted by the inventor, Gabriel Danziger, in Moshav Mishmar Hashiva, Israel. The objective of the breeding program is to develop a new *Petunia* variety with a mounded plant habit and large inflorescence with unique coloration.

The new *Petunia* cultivar originated from a cross-made in a controlled breeding program by the inventor, Gabriel Danziger, in 2006, in Moshav Mishmar Hashiva, Israel. The female or seed parent is *Petunia sensu Wijsman* 'PE-1705' (unpatented), and the male or pollen parent is *Petunia sensu Wijsman* 'PE-99' (unpatented). The new *Petunia* cultivar 'DANRAY5' was discovered and selected by the inventor, Gabriel Danziger, as a single flowering plant within the progeny of the stated cross in a controlled environment in Moshav Mishmar Hashiva, Israel.

Asexual reproduction of the new *Petunia* cultivar by vegetative cuttings used in propagation was first performed in April of 2007 in Moshav Mishmar Hashiva, Israel, and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be unique characteristics of 'DANRAY5' which in combination distinguish this *Petunia* as a new and distinct cultivar:

1. mounded growth habit;
2. large in size, red-colored flowers;
3. high rate floriferous;

4. early to bloom with long bloom period; and
5. suitable for patios and outdoor beddings.

Plants of the new *Petunia* 'DANRAY5' differ from plants of the parents, *Petunia sensu Wijsman* 'PE-1705' (unpatented) and *Petunia sensu Wijsman* 'PE-99' (unpatented) in the characteristics described in Table 1.

TABLE 1

| Characteristic | New Cultivar 'DANRAY5' | Female Parent 'PE-1' (unpatented) | Male Parent 'PE-99' (unpatented) |
|---|---|---|---|
| Plant shape | Mounded | Trailing | Upright |
| Plant size | Height: About 25 cm Spread: About 35 cm | Height: About 20 cm Spread: About 40 cm | Height: About 25 cm Spread: About 30 cm |
| Growth habit | Medium | Strong | Medium |
| Flower size | Depth: About 4 cm Diameter: About 6 cm | Depth: About 4 cm Diameter: About 6.5 cm | Depth: About 4 cm Diameter: About 5 cm |
| Flower color | Red | Red with clear white center | Red |
| Flowering time | Early | Late | Early |

Of the many commercial cultivars known to the present inventor, the most similar in comparison to the new *Petunia* 'DANRAY5' is the *Petunia sensu Wijsman* 'DANCAS110' (patented, U.S. Plant Pat. No. 17,288), in the characteristics described in Table 2:

TABLE 2

| Characteristic | New Cultivar 'DANRAY5' | Comparison Cultivar 'DANCAS110' (patented) |
|---|---|---|
| Plant shape | Mounded | Mounded, bushy |
| Plant size | Height: About 25 cm Spread: About 35 cm | Height: About 25 cm Spread: About 50 cm |
| Flower size | Depth: About 4 cm Diameter: About 6 cm | Depth: About 3 cm to 3.5 cm Diameter: About 4 cm to 5 cm |
| Flower color | Red | Yellow |

BRIEF DESCRIPTION OF THE PHOTOGRAPHS

The accompanying photographs illustrate the overall appearance of the new *Petunia* cultivar 'DANRAY5' showing the colors as true as is reasonably possible with colored reproductions of this type. Colors in the photographs may differ slightly from the color value cited in the detailed botanical description, which accurately describe the color of 'DANRAY5'.

DETAILED BOTANICAL DESCRIPTION

Figure 1:
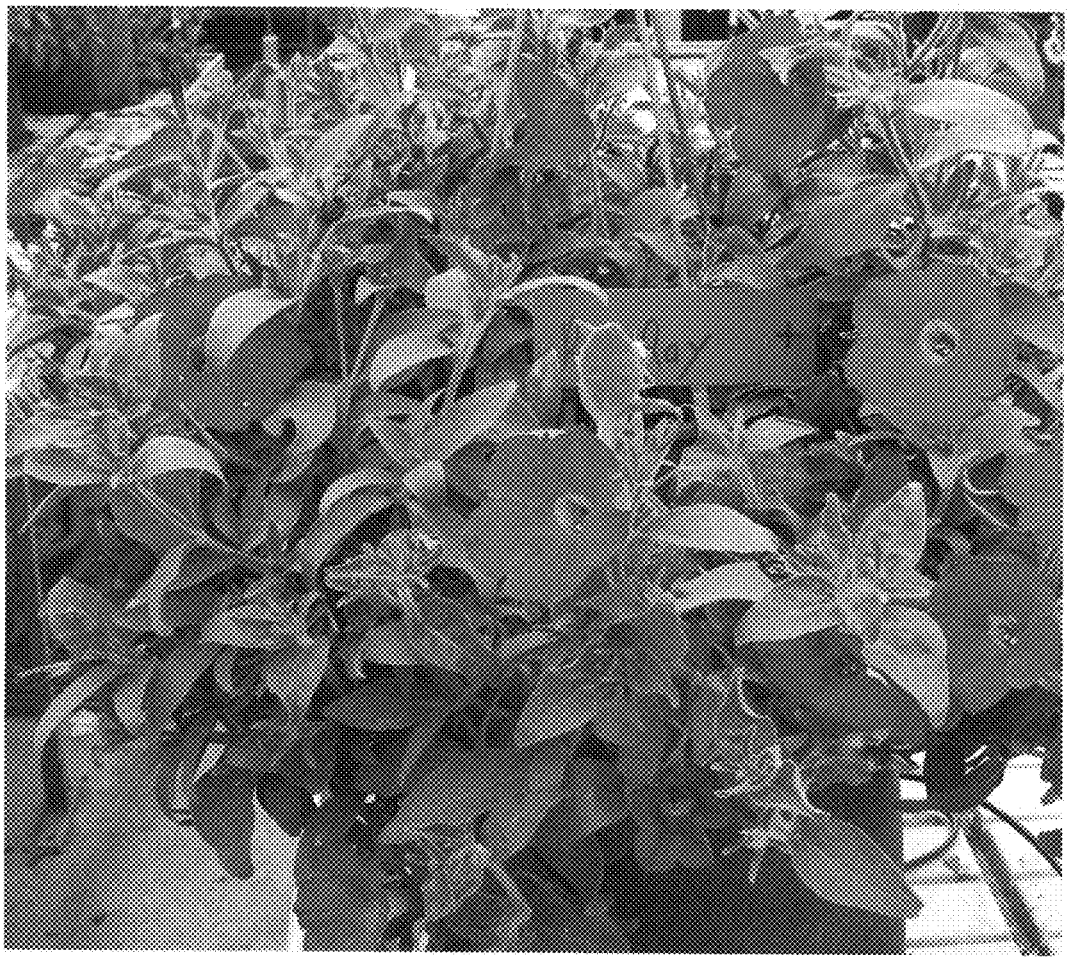
FIG. 1 shows a side view perspective a typical flowering plant of 'DANRAY5' in a 13 cm pot, at 10 weeks after planting.
Figure 2:
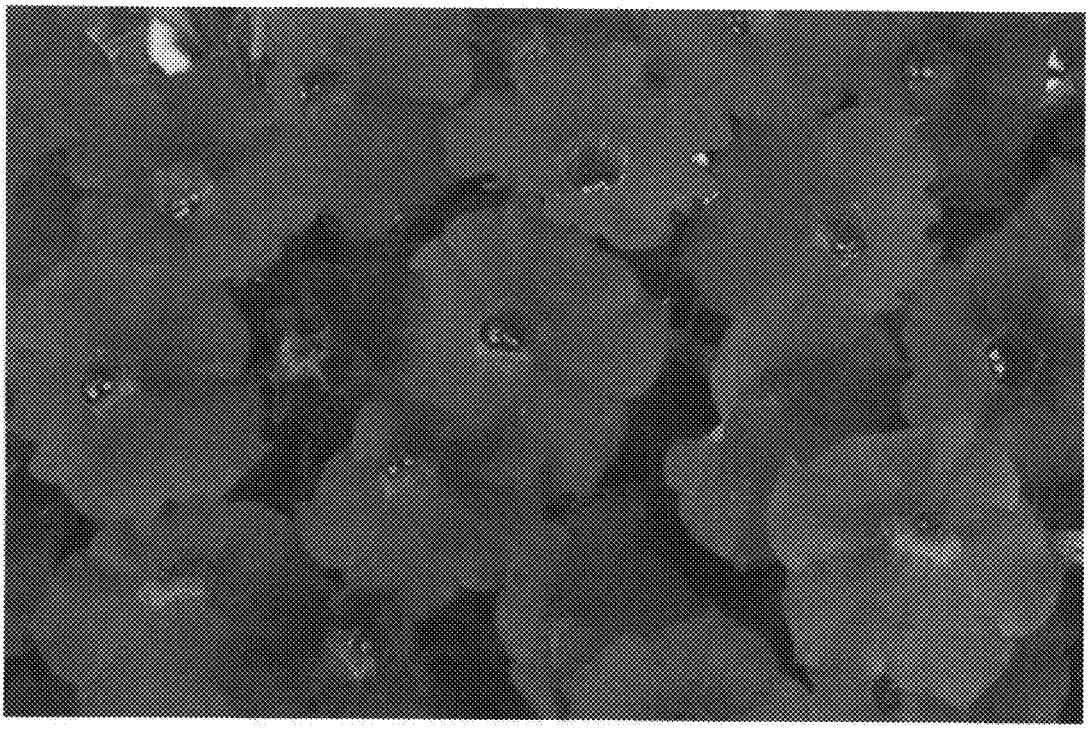
FIG. 2 shows a close-up view of the typical flowers of 'DANRAY5' at 10 weeks after planting.

The new *Petunia* 'DANRAY5' has not been observed under all possible environmental conditions. The phenotype of the new cultivar may vary with variations in environment such as temperature, light intensity, and day length without any change in the genotype of the plant.

Plants of 'DANRAY5' are grown outdoors in a moderate climate, and grown indoors during the winter. Irrigation and fertilization are needed on a regular basis. For optimal growth, grow plants of 'DANRAY5' in full sunlight. Plants of 'DANRAY5' are fully-grown in 3 months when grown in full sunlight, and bloom all year-round in a moderate climate.

The aforementioned photographs, together with the following observations, measurements and values describe the new *Petunia* 'DANRAY5' as grown in a greenhouse in Moshav Mishmar Hashiva, Israel, under conditions which closely approximate those generally used in commercial practice.

Color references are made to The Royal Horticultural Society Color Chart (R.H.S.), 2001 edition, except where general colors of ordinary significance are used. Color values were taken under daylight conditions at approximately (time) 12:00 noon in Moshav Mishmar Hashiva, Israel. The age of the plant described is 10 weeks from planting.

Classification:

*Botanical.*—*Petunia sensu Wijsman.*

Parentage:

*Female or seed parent.*—*Petunia sensu Wijsman* 'PE-1705' (unpatented).

*Male or pollen parent.*—*Petunia sensu Wijsman* 'PE-99' (unpatented).

Optimal growth conditions:

*Light intensities.*—Full sunlight.

*Temperature.*—Day: 22° C. to 32° C. Night: 15° C. to 20° C.

*Temperature tolerance.*—Tolerant to a low temperature of about 5° C. and tolerant to a high temperature of about 40° C.

Foliage:

*Arrangement.*—Alternate, sessile.

*Overall shape of leaf.*—Elliptic.

*Apex.*—Rounded (Obtuse).

*Base.*—Cuneate.

*Length.*—About 3.5 cm to 6 cm.

*Width.*—About 2 cm to 3.5 cm.

*Margin.*—Entire.

*Texture.*—Upper and under surfaces: Pubescent.

*Pubescence.*—Upper and under surfaces: Puberulent.

*Color of upper surface.*—Immature and mature leaves: Green, RHS 139A.

*Color of under surface.*—Immature and mature leaves: Green, RHS 137C.

*Venation pattern.*—Pinnate.

*Venation color.*—Upper and under surfaces: Green, RHS 137D.

Inflorescence:

*Flower longevity.*—About 3 to 6 days.

*Flower size.*—Diameter: About 6.5 cm. Depth: About 4 cm.

*Floral tube.*—

*Diameter.*—1.0 cm to1.5 cm at the corolla surface.

*Flower shape/type.*—Salverform.

*Average number of flowers per lateral branch.*—About 5 to 10.

*Fertilization.*—A balanced fertilizer with level N: P: K=5:3:8, using 250–300 ppm Nitrogen.

*Growth regulators.*—Not necessary in Israel climate.

Propagation:

*Type.*—Tip cuttings of side shoots.

*Rooting habit and description.*—Easy to root; root from cutting base.

*Time to initiate roots.*—About 5 to 10 days at 20° C.

*Time to produce a rooted cutting.*—About 14 days at 20° C.

Plant:

*General appearance and form.*—Height: About 25 cm. Spread: About 35 cm.

*Growth habit.*—Mounded.

*Growth rate.*—Fully grown plant in 3 months.

*Branching habit and description.*—Freely branching, typical to *Petunia* species.

*Flowering response.*—Indifferent to day length.

*Flowering season.*—Year round in moderate climate.

*Winter hardiness/weather tolerance.*—Frost tender. Plants may be damaged by temperatures below 5° C.

*Lastingness of the individual bloom.*—3 to 6 days.

*Fragrance.*—None.

Stem description:

*Quantity per plant.*—About 20.

*Length.*—About 20 cm to 40 cm.

*Diameter.*—About 0.2 cm to 0.5 cm.

*Strength.*—Strong.

*Branching.*—Freely.

*Texture.*—Pubescent.

*Internodes length.*—About 2 cm to 4 cm.

*Internodes and stem color.*—Yellow-green, RHS 144C.

*Petals.*—Number: 5; all 5 petals are united. Length: About 5 cm to 6.5 cm (from edge of the petal up to the base of floral tube). Width: About 2.5 cm across. Shape: Corolla united with 5 lobes and a long straight tube. Apex: Rounded (Obtuse). Margin: Entire. Texture: Upper and under surfaces: Glabrous. Color (when opening and when fully opened): Upper and Under Surfaces: Greyed-red, RHS 181A, with red, RHS 42A.

*Sepals.*—Number: 5. Length: About 1.5 cm to 2.2 cm. Width: About 0.4 cm to 0.7 cm. Shape: Oblong. Apex: Truncate. Margin: Entire. Texture: Upper and under surfaces: Pubescent. Color: Upper surface: Green, RHS 137A. Under surface: Green, RHS 139B.

*Bud.*—Rate of opening: About 2 to 4 days. Shape: Tubular. Length: About 3 cm to 5 cm. Diameter: About 0.6 cm to 1 cm. Texture: Pubescent. Color: Greyed-red, RHS 180C.

*Peduncle.*—Length: About 2 cm to 2.5 cm. Diameter: About 2 mm to 3 mm. Texture: Pubescent. Color: Yellow-green, RHS 144C.

Reproductive organs:

*Androecium.*—Stamen: Number: 5. Length: 1.5 cm. Color: Green, RHS 139D. Anther: Shape Round. Length: About 1 mm. Color: Yellow, RHS 11C. Filaments: Length: About 14 mm. Color: White, RHS 155C. Pollen: Amount: Abundant. Color: RHS 11C. Pollination requirements: None.

*Gynoecium.*—Pistils: Quantity: 1. Length: About 15 mm. Color: Yellow-green, RHS 144B. Stigma: Shape: Undulate. Width: About 2 mm. Color: Yellow-green, RHS 144A.

*Style.*—Shape: Terete. Length: About 15 mm. Color: Yellow-green, RHS 144B.

*Ovary.*—Shape: Narrowly Conical. Position: Superior. Length: About 4 mm. Width: About 3 mm at the base. Color: Yellow-green, RHS 144A.

Seeds:

*Quantity per fruit.*—About 200 to 400.

*Shape.*—Round.

*Length.*—About 0.5 mm.

*Width.*—About 0.5 mm.

*Texture.*—No hair.

*Color.*—Black, RHS 202B.

Fruit:

*Number.*—Few, when naturally pollinated.

*Type.*—Capsule.

*Shape.*—Ellipsoid.

*Length.*—About 9 mm.

*Width.*—About 6 mm.

*Texture.*—Glabrous.

*Color.*—Yellow-green, RHS 144B.

Disease/pest resistance: Resistance to disease and pests common to *Petunia* has not been tested on plant grown under commercial conditions.

Disease/pest susceptibility: Susceptibility to disease and pests common to *Petunia* has not been observed on plant grown under commercial conditions.

Temperature tolerance: Plants of the new *Petunia* have exhibited good tolerance to draught, rain and wind; however, flowering may cease during hot periods (temperatures above 45° C.). Low temperature tolerance to 5° C.

What is claimed is:

1. A new and distinct *Petunia* plant named 'DANRAY5', substantially as illustrated and described herein.

* * * * *